(12) United States Patent
Nambu

(10) Patent No.: US 6,231,844 B1
(45) Date of Patent: May 15, 2001

(54) NONIONIC SURFACTANT FOAMING AGENTS FOR FOAMING COSMETIC COMPOSITIONS

(75) Inventor: Takanori Nambu, Nada-ku (JP)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 08/930,919

(22) PCT Filed: Mar. 20, 1996

(86) PCT No.: PCT/US96/03938

§ 371 Date: Oct. 13, 1997

§ 102(e) Date: Oct. 13, 1997

(87) PCT Pub. No.: WO96/32093

PCT Pub. Date: Oct. 17, 1996

(30) Foreign Application Priority Data

Apr. 13, 1995 (AU) .................................. PN 2395

(51) Int. Cl.[7] .................. A61K 9/12; A61K 7/06
(52) U.S. Cl. .................. 424/70.31; 424/45; 424/47; 424/70.19; 424/70.21; 424/70.22; 424/70.27; 424/70.15; 424/70.16; 424/70.12; 514/937; 514/945
(58) Field of Search .................. 424/45, 400, 47, 424/70.19, 70.21, 70.22, 70.27, 70.31, 70.15, 70.16, 70.12; 514/945, 937

(56) References Cited

U.S. PATENT DOCUMENTS 4,122,159 * 10/1978 Madrange et al. .
4,900,326 * 2/1990 Grollier .
5,002,680 * 3/1991 Schmidt et al. .
5,182,407 * 1/1993 Sebag .

FOREIGN PATENT DOCUMENTS 37 40 926   6/1989 (DE) .
96/3209    10/1996 (WO) .

OTHER PUBLICATIONS

62–Essential Oils, Cosmetics, vol. 117, 1992, p. 427.
62–Essential Oils, Cosmetics, vol. 123, 1995, p. 665.
Chemical Abstracts, vol. 120, 1994, p. 648.

* cited by examiner

*Primary Examiner*—Raj Bawa
(74) *Attorney, Agent, or Firm*—Holly D. Kozlowski; T. David Reed; Stephen T. Murphy

(57) ABSTRACT

Cosmetic foaming compositions and hair mousse compositions employ a foaming agent comprising a mixture of first and second nonionic surfactants and having a total HLB as measured by the Griffin method of at least 12. The first nonionic surfactant is selected from defined polyoxyethylene alkyl ether surfactants, polyoxyethylene alkenyl ether surfactants, polyoxypropylene polyoxyethylene ether surfactants, and mixtures thereof; and the second nonionic surfactant is selected from defined polyoxyethylene long chain alkyl fatty acid or benzene ether surfactants, polyoxyethylene ether surfactants, polyoxypropylene ether surfactants, and mixtures thereof.

17 Claims, No Drawings

NONIONIC SURFACTANT FOAMING AGENTS FOR FOAMING COSMETIC COMPOSITIONS

TECHNICAL FIELD

The present invention relates to a foaming agent comprising at least a polyoxyethylene and/or polyoxypropylene type of nonionic surfactant which has a total HLB by Griffin method of at least 12, which provides clear and stable concentrates and voluminous and stable foaming, and smooth and mild touch to foaming cosmetic compositions, with improved less flaking tendency. In particular, the present invention relates to leave-on hair mousse products comprising this foaming agent.

BACKGROUND

Cosmetic compositions such as shaving creams, hair mousses, spray foams, foaming lotions and foaming creams are aimed to be dispensed or sprayed as foams and applied on the human skin or hair. These products are described in the present invention as "leave-on foaming cosmetic products". One common characteristic desired for these leave-on foaming cosmetic products is a foam having favorable characteristics to the consumer such as voluminous and stable foaming, with smooth and mild touch to the skin and hair.

Leave-on foaming cosmetic compositions for hair are usually referred to as "mousses", which term will be used in the present invention. Hair mousses were born in Europe in the early 1980s. Hair mousses are fundamentally an aerosol foam, however, non-aerosol foams are also known. The general appeal of hair mousses can be largely attributed to the ease of application and controlled amount of product which are possible from mousse formulations. Hair mousse compositions are generally dispensed by a compressible dispenser or a valve and applied to the user's hand or a specifically designed comb and spread through the hair. Alternatively, hair mousse compositions can be directly applied to the hair by dispensing through nozzles. Hair mousses are formulated for the purpose of styling, setting, and arranging, or for other purposes such as shampooing, conditioning, treating, dyeing, and combinations thereof.

In recent years, some consumers have expressed a desire to have "alcohol-free" hair mousse products because of concerns relating to drying of the hair, or concerns of volatile solvents being emitted to the environment. In this context, alcohol refers to volatile primary alcohols having about 1 to 6 carbons, particularly ethanol. Alcohol is used in mousses for a number of reasons. First, the presence of volatile alcohol can aid styling by decreasing drying time. However, it is assumed that this drying has raised the concerns of some consumers that alcohol is also drying hair. Second, alcohol aids foam breakage as the mousse is spread throughout the hair. It is known that foam breakage is a result of the ability of alcohol to act as a defoaming agent. Third, alcohol itself improves product preservation. Fourth, alcohol enhances the compatibility of the concentrate with the propellant, and acts as a solubility bridge between the resin and the water base. Fifth, alcohol is a good solvent for dissolving oil base ingredients such as conditioning fatty alcohols. Consequently, elimination of alcohol from the formulation may affect product performance. Thus, there is a desire to provide a foaming agent which can be used in hair mousse compositions with or without alcohol.

The species and level of preservatives are also known to affect product performance. Preservatives such as DMDM Hydantoin (dimethylol dimethyl hydantoin) and Kathon CG (mixture of methylchloro-isothiazolinone and methyl isothiazolinone) are known as effective preservatives at low levels, however, are not approved for use in leave-on cosmetic products in a number of countries. Phenoxyethanol and EDTA are widely accepted for use, however, are not satisfactorily effective at low levels. Parabens such as methyl paraben, propyl paraben, butyl paraben, and Liqua-Par oil (mixture of isobutyl paraben, isopropyl paraben, and butyl paraben) are also widely accepted for use. However, because parabens are lipophilic, they cannot dissolve in water, and thus have some formulation constraints. Methyl paraben and propyl paraben are difficult to formulate at high levels, for they are solid at room temperature. Thus, there is also a desire to provide a foaming agent which can be used in hair mousse compositions in combination with a wide range of preservatives.

The type of propellants are also known to affect product performance. It is known that fluorohydrocarbons such as difluoroethane 152a (supplied by DuPont) can be used for a wide range of formulations. Propane and dimethyl ether can also be used for a wide range of formulations. However, propane is relatively combustible. Dimethyl ether when used at high levels can be corrosive. LPG (liquefied petroleum gas) is a mixture of mainly iso-butane, n-butane, and propane, and is available in different pressure grades. LPG is a relatively safe propellant, however, have some formulation constraints. Thus, there is also a desire to provide a foaming agent which can be used in hair mousse compositions in combination with a wide range of propellants.

Evaluation of product performance for hair mousse compositions vary depending on the purpose and concept of the product. In evaluating the performance of a hair mousse, one generally considers properties seen in three major stages; the properties of the foam upon dispensing from the package, the properties of the foam upon applying to the hair, and properties of the end results to the hair. Properties considered upon dispensing include volume of foam and foam expansion speed. It is known that when foam expansion is slow or delayed, "pooling" of the product occurs. Properties considered upon applying to the hair include stability and breakability of the foam, non-soapiness, smoothness, softness, creaminess, and stickiness. Properties considered on the end results to the hair include style control, dry or wet feel of hair, washability, shine, moisturizing, conditioning, anti-static, and brushing.

An attempt to achieve the above requirement, co-pending, commonly-assigned U.S. application Ser. No. 08/154,231(Y. Chen and T. Nambu) filed Nov. 18, 1993 discloses a foaming agent for leave-on foaming cosmetic composition comprising an amphoteric surfactant and an amine oxide.

However there remains a need for foaming cosmetic compositions contain no amine oxide. In Europe, there is an interest in a formula that does not use amine oxide for safety reasons.

Further there remains a need for foaming cosmetic compositions having improved clear and stable concentrations, especially, in the presence of a polymer, such as cationic type of water soluble polymer in the compositions.

OBJECT OF THE INVENTION

It is an object of the present invention to provide a foaming agent which foams by being dispensed or sprayed, and provides voluminous and stable foaming, smooth and mild touch, and styling/conditioning effect to foaming cosmetic compositions.

It is also an objective of the present invention to provide a foaming cosmetic composition which provides a stable and clear concentration for better product stability.

It is further an object of the present invention to provide a foaming cosmetic composition such as a hair mousse composition comprising said foaming agent which provides a foam having appropriate foam breakdown (foam breakability) under shear and is easy to spread on hair, has a smooth, soft and creamy texture, and has a mild touch.

It is further an object of the present invention to provide a foaming cosmetic composition such as a hair mousse composition comprising said foaming agent which can be formulated in combination with a wide range of solvents, preservatives, and propellants.

It is further an object of the present invention to use a surfactant system that does not contain amine oxide.

It is further an object of the present invention to provide a foaming cosmetic composition such as a hair mousse composition comprising said foaming agent which provides quick, voluminous foam expansion and reduced pooling upon dispensing.

It is further an object of the present invention to provide a hair mousse composition comprising said foaming agent which provides good style control, conditioning effect, and good feel to the hair, with less flaking tendency.

SUMMARY OF THE INVENTION

The present invention relates to a foaming agent comprising at least a polyoxyethylene and/or polyoxypropylene type of nonionic surfactant which has a total HLB by Griffin method of at least 12, which foams by being dispensed or sprayed, and provides improved foaming characteristics to foaming cosmetic compositions.

The present invention also relates to a foaming cosmetic composition such as a hair mousse composition comprising the foaming agent and further comprising a polymer such as cationic type of water soluble polymer, but not limited to cationic type, a solvent and a propellant.

In a particularly preferred embodiment of the present invention, the hair mousse composition comprises the foaming agent which comprises at least a polyoxyethylene and/or polyoxypropylene type of nonionic surfactants which has a total HLB by Griffin method of at least 12, from 0.005% to 5%, and further comprises a polymer, a solvent, a preservative, and a propellant.

DETAIL DESCRIPTION OF THE INVENTION

The present invention relates to a foaming agent for use in a foaming cosmetic composition which foams by being dispensed or sprayed, comprising at least a polyxyethylene and/or polyoxy propylene type of nonionic surfactant which has and total HLB by Griffin method of at least 12. In another word, the present invention relates to a foaming agent for use in a foaming cosmetic composition which foams by being dispensed or sprayed, comprising at least a nonionic surfactant comprises polymer units selected from polyoxyethylene, polyoxypropylene, and mixtures thereof The present invention also relates to a foaming composition such as a hair mousse composition comprising the foaming agent and further comprising a polymer, a solvent and a propellant.

All percentages and ratios are based on weight unless otherwise specified. The total of components except for propellant is defined as a concentrate. For non-aerosol products containing no propellant, the concentrate is equal to the entire composition.

FOAMING3 AGENT

The foaming agent of the present invention comprises at least a polyxyethylene and/or polyoxy propylene type of nonionic surfactant which has a total HLB by Griffin method of at least 12. In the present invention, HLB is measured by Griffin method as follows: For polyhydric alcohols and fatty acid esters, HLB is calculated by the following calculated general formula(i):

$$HLB = 20(1 - S/A) \qquad (i)$$

wherein;
S is saponification value of esters,
A is acid value of fatty acids;
For cases which saponification value is not clear, HLB is calculated by the following general formula(ii):

$$HLB = (E+P)/5 \qquad (ii)$$

wherein;
E is weight percentage of ethylene oxide,
P is weight percentage of polyhydric alcohol; and
For cases which polyoxyethylene is the only hydrophilic group, HLB is calculated by the following general formula (iii):

$$HLB = E/5 \qquad (iii)$$

E is weight percentage of ethylene oxide.

When comprised in foaming cosmetic compositions such as hair mousses, the foaming agent of the present invention preferably comprises at least a polyxyethylene and/or polyoxy propylene type of nonionic surfactant which has and total HLB by Griffin method of at least 12, from 0.005% to 5%, more preferably 0.005% to 3%. When the foaming agent of the present invention is applied to foaming cosmetic composition, it provides clear and stable concentrates and voluminous and stable foaming, and smooth and mild touch to foaming cosmetic compositions, with improved less flaking tendency. Other components of a foaming agent and include solvents such as water, lower alcohol, polyhydric alcohols, and mixture thereof.

NON-IONIC SURFACTANT

Polyoxyethylene Alkyl Ether
Polyoxyethylene alkyl ether is polyethylene glycol ether of alkyl alcohol. The polyoxyethylene alkyl ether surfactant can be the following general structure;

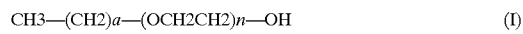

$$CH_3-(CH_2)a-(OCH_2CH_2)n-OH \qquad (I)$$

wherein;
a has an average value from 9 to 21,
n has an average value from 2 to 200;
Polyoxyethylene Alkenyl Ether
The polyoxyethylene alkenyl ether surfactant can be the following general structure;

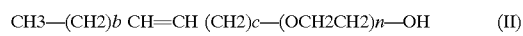

$$CH_3-(CH_2)b\ CH=CH\ (CH_2)c-(OCH_2CH_2)n-OH \qquad (II)$$

wherein;
b has an average value from 1 to 10,
c has an average value from 1 to 10,
n has an average value from 2 to 200;
Polyoxypropylene polyoxyethylene Alkyl or alkenyl or iso-alkyl or iso-alkenyl or dimethylpolysiloxane Ether
The polyoxypropylene polyoxyethylene alkyl or alkenyl or iso-alkyl or iso-alkenyl or dimethylpolysiloxane Ether surfactant can be the following general structure;

$$R1\text{—}(OCH(CH3)CH2)x\text{—}(OCH2CH2)y\text{—}OH \quad (III)$$

wherein;

R1 is alkyl alkenyl groups or isoalkyl alkenyl groups or dimethylpolysiloxane derivatives, x has an average value from 2 to 100, y has an average value from 2 to 100;

Polyoxyethylene Long chain alkyl fatty acid or dimethylpolysiloxane or benzene derivatives Ether The polyoxyethylene long chain alkyl fatty acid or benzene derivatives ether surfactant can be the following general structure;

(4) a polyoxyethylene Long chain alkyl fatty acid or benzene derivatives ether surfactant having the following general structure (IV):

$$R2\text{—}(OCH2CH2)n\text{—}OH \quad (IV)$$

wherein;

R2 can be selected from the group consisting of castor oil triglyceride castorate, cholesterol, coconut oil triglyceride cocoate, alkyl phenol, glyceryl laurate, glyceryl oleate, glyceryl cocoate, glyceryl Isostearate, glyceryl stearate, hydrogenated castor oil triglyceride hydrogenated castorate, hydrogenated lanolin, nonyl phenyl and dimethylpolysiloxane derivatives, n has an average value from 2 to 200;

Polyoxyethylene Dialkyl or iso-alkyl or alkenyl Ether

The polyoxyethylene Dialkyl, or iso-alkyl, or alkenyl ether surfactant can be the following general structure;

$$R3\text{—}C(O)\text{—}(OCH2CH2)n\text{—}O\text{—}C(O)\text{—}R4 \quad (V)$$

wherein;

R3 and R4 are respectively selected from the group consisting of alkyl groups, iso-alkyl groups and alkenyl groups, n has an average value from 2 to 200;

Polyoxypropylene Alkyl, iso-alkyl, alkenyl or long chain alkyl fatty acid Ether

The polyoxypropylene Alkyl, iso-alkyl, alkenyl or long chain alkyl fatty acid ether surfactant can be the following general structure;

$$R5\text{—}(OCH(CH3)CH2)nOH \quad (VI)$$

wherein;

R5 is alkyl groups, isoalkyl groups or alkenyl groups, n has an average value of 2 to 200.

FOAMING COSMETIC COMPOSITIONS

A foaming cosmetic composition of the present invention comprises a concentrate which is a foamable liquid which produces a foam when mixed an external source of air or gas, and is dispensed as a foam.

A concentrate (by weight) of the foaming cosmetic composition of the present invention comprises 0.005–20%, more preferably 0.005–10%, most preferably 0.005–6%, of the foaming agent.

Solvent

The foaming cosmetic compositions further preferably comprises a solvent for the foaming agent. Solvents used in a foaming cosmetic composition of the present invention are selected depending on variables such as the remainder components, viscosity, and desired foaming characteristic of the composition.

When comprised in hair mousses, the solvent is preferably comprised at a level of 60–99%, more preferably 80–99%, most preferably 85–98% of the concentrate.

Non-limiting examples of solvents useful in the present invention are: water, lower alcohols having 1 to 6 carbons such as ethanol and isopropanol, and polyhydric alcohols such as propylene glycol, hexylene glycol, glycerin, and propane diol, and mixtures thereof.

Propellant

The foaming cosmetic compositions further preferably comprises a propellant so mixing with the concentrate to foam the foam.

Propellants when used in a foaming cosmetic composition in the present invention are selected depending on variables such as the remainder components, the package, and how the product is designed to be used (standing or invert).

When comprised in hair mousses, the propellant is preferably comprised at a level of 0–60%, more preferably 0–30% of the entire composition. When no propellant is used, the hair mousse composition is usually provided in a package equipped with an air or gas mixing device. Non-limiting examples of propellants useful in the present invention are: fluorohydrocarbons such as difluoroethane 152a (supplied by DuPont), dimethyl ether, carbon dioxide, nitrogen, and hydrocarbons such as propane, iso-butane, n-butane, and mixtures of hydrocarbons such as LPG (liquefied petroleum gas).

When used with a propellant, the components usually must be contained under pressure in a suitable vessel, such as a pressed dispensing package which is well known in the art(for example, a package for Vidal Sassoon Styling Mousse Extra Body/The Procter & Gamble Company).

Optional components

Optional components can be included in the foaming cosmetic compositions of the present invention, depending on the needs of the product. Non-limiting examples of such optional components include additional surfactants, ultraviolet and infrared screening and absorbing agents, hair conditioning agents, skin conditioning agents, perfume, color, pH adjusters, polymers, dyes, vitamins, proteins, plant extracts, and nutrients.

A foaming cosmetic composition such as a hair mousse compositions can comprise a polymer for hair styling and conditioning, and a preservative, and can further comprise other optional components.

Polymer

A foaming cosmetic composition such as a hair mousse compositions may further comprise a polymer. Such polymer comprise cationic, nonionic, anionic, and amphoteric polymers. Polymer is typically included by weight at a level of 0–15%, preferably 0–10% of the concentrate.

Polymers suitable for use herein include any polymers soluble or colloidally dispersible in the aqueous phase (if water is the only solvent in the aqueous phase, the polymer should be soluble or dispersible in water; if an optional cosolvent such as ethanol is present the polymer should be soluble or dispersible in the combined solvent system). Solubility/dispersibility is determined at ambient conditions of temperature and pressure (25° C. at 1At). Polymers for use in the compositions of the present invention include cationic, anionic, nonionic, and amphoteric resins.

Non-limiting examples of cationic polymers useful in the present invention include quatemized cellulose ethers such as Polyquatemium 10 (hydroxyethylcellulose hydroxypropyl trimethylammonium chloride ether) under the trade name Ucare Polymer LR and Polyquatemium 4 (hydroxyethylcellulose dimethyidiallyl ammonium chloride copolymer) under the trade name Celquat, quatemized vinyl pyrrolidonelalkylaminoacrylate or methacrylate copolymers such as Polyquatemium 11 (polyvinylpyrrolidone N,N'-dimethylaminoethylmethacrylic acid copolymer diethyl sulfate salt) under the trade name Gafquat, methylvinylimidazolium vinylpyrrolidone quaternary ammonium copolymers commercially available under the trade name Luviquat, vinylmethyl ether ethyl maleate copolymer (PVMIMA copolymer), PVPNA copolymer under the trade name Luviskol, polyvinyl alcohol, copolymers of polyvinylalcohol and crotonic acid, copolymers of polyvinylalcohol and maleic anhydride, hydroxypropyl cellulose, hydroxypropyl guar gum, sodium polystyrene sulfonate, polyvinylpyrrolidone ethylmethacrylate methacrylic acid terpolymer, octylacrylamide acrylate butylaminoethyl methacrylate copolymers, N-methacryloyl ethyl-N,N'-dimethyl ammonium gamma-N-methyl carboxy betaine butyl methacrylate copolymer under the trade name Yukaformer AM-75, and mixtures thereof.

Other examples of cationic polymers include silicone-grafted copolymers (including mixtures of such copolymers), comprising silicone covalently bonded to the polymer backbone (i.e. silicone chains are grafted to the backbone), and are derived by polymerization of a combination of nonionic, nonquatemizable, water soluble monomers and nonionic, quatemizable monomers. The silicone macromers will generally be incorporated into the polymer by conducting the polymerization of the above two types of monomers also in the presence of silicone macromer, i.e. silicone containing monomers.

The silicone macromer-grafted copolymers hereof will have a polymeric backbone with a Tg of from about 30° C. to about 140° C. The silicone macromer-containing copolymers have an organic polymeric backbone, preferably a vinyl backbone or other carbon-based backbone derived from ethylenically unsaturated polymerizable monomers. The polymers are derived by polymerization of: from about 2% to 15%, by weight, of silicone macromers; from about 5% to 40%, by weight, anionic, quatemizable monomers; and from about 30% to 60%, by weight, of non-ionic, water soluble, nonquatemizable monomers. At least 5% of the monomers, by weight are quatemized.

The quatemizable nonionic monomers hereof include quaternizable, amino-functional ethylenically unsaturated monomers, such as the amino functional derivatives of styrene, acrylamides, methacrylamides, (meth)acrylates such as $C_1$–$C_5$ alkyl esters of acrylic acid and methacrylic acid.

Examples of such monomers include: (i) p-dimethylaminomethyistyrene, p-dimethylaminoethylstyrene; (ii) dimethylaminomethyl acrylamide, dimethylaminopropyl acrylamide, dimethylaminopropyl methacrylamide, dimethylaminomethyl methacrylamide, dimethylaminoethyl (meth)acrylate, diethylaminoethyl (meth)acrylate, dimethylaminopropyl (meth)acrylate, and dimethylaminopropyl (meth) acrylamide.

Examples of nonionic, nonquatemizable, water soluble monomers include acrylamides, methacrylamides, (meth) acrylates, cinamides, vinyl alcohols, vinyl pyrrolidones, vinyl oxazolidones, and derivatives thereof Specific examples include acrylamide, methacrylamide, mono- and di- $C_1$-$C_6$ alkyl (meth)acrylamides, such as dimethylacrylamide, dimethylmethacrylamide, isopropylacrylamide, t-butylacrylamide, isopropylmethacrylamide, diacetone acrylamide, mono- and di- $C_1$–$C_{20}$ alkyl (meth) acrylamides, such dimethylacrylate, t-butyl acrylate, t-butyl methacrylate, isopropyl methacrylate, stearyl methacrylate, cetyl methacrylate, acrylglycinamide, methacrylglycinamide, vinyl alcohol, vinyl pyrrolidone, vinyl oxazolidone, vinylmethoxazolidone, and poly(ethylene glycol) phenyl ether (meth)acrylate.

Other examples of cationic polymers are cationic guar gums, for example, hydroxypropyltrimethylammonium guar gum, quatemized cellulose ethers such as copolymers of hydroxyethylcellulose with diallyidimethyl ammonium chloride or with trimethyl ammonium substituted epoxides, homopolymers of lower alkylamino alkyl acrylate or methacrylate monomers (e.g. dimethyl aminoethylmethacrylate) and copolymers thereof with compatible monomers such as N-vinylpyrrolidone or with methacrylate derivatives such as methyl, ethyl, abietyl and oleyl methacrylates and mixtures thereof and/or with alkyl acrylates such as methyl and butyl acrylates and mixtures thereof, copolymers of dimethyidiallyl ammonium chloride and acrylamide, homopolymers of dimethyldiallyl ammonium chloride, vinylimidazolium/vinyl pyrrolidone copolymers, and mixtures thereof.

Polycationic hair conditioning polymers can be derived from polymerizable cationic starting monomers, or from polymerizable nonionic monomers which are modified subsequent to polymerization to be of cationic character.

Examples of the cationic monomers include:

(i) monomers derived from acrylic acid or methacrylic acid, which is referred to hereinafter collectively as (meth)acrylic acid, and a quatemized epihalohydrin product of a trialkyl amine having 1 to 5 carbon atoms in the alkyl group such as (methy)acryloxypropyltrimethylammonium choride and (meth)acryloxypropyltriethylammonium bromide;

(ii) amine derivatives of (meth)acrylic acid or amine derivatives of (meth)acrylamide derived from (meth)acrylic acid or (meth)acrylamide and a dialkylalkanolamine have $C_1$–$C_4$ alkyl groups such as dimethylaminoethyl (meth)acrylate, diethylaminoethyl (meth)acrylate, dimethylaminopropyl (meth)acrylate, or dimethylaminopropyl (meth)acrylamide; and (iii) derivatives of the products of the group (ii) above by (1) neutralization with an inorganic or organic acid, such as hydrochloric acid, or lactic acid, (2) modification with a halogenated alkyl, such as methyl chloride, ethyl chloride, methyl bromide, or ethyl iodide, (3) modification with a halogenated fatty acid ester such as ethyl monochloroacetate, or methyl monochloropropionate, and (4) modification with a dialkyl sulfate such as dimethyl sulfate, or diethyl sulfate.

Furthermore, the cationic unsaturated monomers include amine derivatives of allyl compounds such as diallyidimethylammonium chloride and the like as well as vinylimidazolium quaternary ammonium monomers.

These cationic unsaturated monomers can be polymerized in cationic form, or as an alternative they can be polymerized in the form of their precursors, which are then modified to be cationic, for example, by a quatemizing agent (eg. ethyl monochloroacetate, dimethyl sulfate, etc.)

Non-limiting examples of polycationic polymers include cationic polysaccharides, homopolymers of dimethyidiallyl ammonium chloride, copolymers of dimethyldiallyl ammonium chloride and acrylamide, cationic amino-functional homopolymers and copolymers derived from acrylic acid and/or methacrylic acid, especially from alkylaminoalkyl acrylate and methacrylate monomers such as dimethylaminoethyl acrylate and methacrylate, polyalkylene imines and ethoxy polyalkylene imines, vinylimidazolium/vinylpyrrolidone quatemary ammonium copolymers, and mixtures thereof.

Non-limiting examples of nonionic monomers are acrylic or methacrylic acid esters of $C_1$–$C_{24}$ alcohols, such as methanol, ethanol, 1-propanol, 2-propanol, 1-butanol, 2-methyl-I-propanol, 1-pentanol, 2-pentanol, 3-pentanol, 2-methyl-I-butanol, 1-methyl-i-butanol, 3-methyl-1-butanol, 1-methyl-i-pentanol, 2-methyl-i-pentanol, 3-methyl-I-pentanol, t-butanol, cyclohexanol, 2-ethyl-i-butanol, 3-heptanol, benzyl alcohol, 2-octanol, 6-methyl-i-heptanol, 2-ethyl-i-hexanol, 3,5-dimethyl-1-hexanol, 3,5,5-trimethyl-1 -hexanol, 1 decanol, 1 -dodecanol, 1 -hexadecanol, 1-octadecanol, and the like, the alcohols having from about 1–24 carbon atoms; styrene; chlorostyrene; vinyl esters such as vinyl acetate; vinyl chloride; vinylidene chloride; acrylonitrile; alpha-methylstyrene; t-butylstyrene; butadiene; cyclohexadiene; ethylene; propylene; vinyl toluene; alkoxyalkyl (meth)acrylate, such as methoxy ethyl (meth)acrylate and butoxyethyl (meth)acrylate; and mixtures thereof. Other nonionic monomers include acrylate and methacrylate derivatives such as allyl acrylate and methacrylate, cyclohexyl acrylate and methacrylate, oleyl acrylate and methacrylate, benzyl acrylate and methacrylate, tetrahydrofurfuryl acrylate and methacrylate, ethylene glycol di-acrylate and -methacrylate, 1,3-butyleneglycol d-acrylate and -methacrylate, diacetonacrylamide, isobornyl (meth)acrylate, and the like.

Non-limiting examples of polar nonionic monomers include acrylamide, N,N-dimethylacrylamide, methacrylamide, N-t-butyl acrylamide, methacrylonitrile, acrylamide, acrylate alcohols (eg. $C_2$–$C_6$ acrylate alcohols such as hydroxyethyl acrylate, hydroxyproxyl acrylate), hydroxyethyl methacrylate, hydroxypropyl methacrylate, vinyl pyrrolidone, vinyl ethers, such as methyl vinyl ether, acyl lactones and vinyl pyridine, allyl alcohols, vinyl alcohols and vinyl caprolactam.

Preservative

Hair mousse compositions can further comprise a preservative. Such preservative is preferably included at a level of 0–5%, more preferably 0–3% of the concentrate.

Non-limiting examples of preservatives useful in the present invention are DMDM Hydantoin (dimethylol dimethyl hydantoin) Kathon CG, (mixture of methylchloroisothiazolinone and methyl isothiazolinone), imidazolidinyl urea, phenoxyethanol, EDTA and its salts, benzyl alcohol, and parabens such as methyl paraben, propyl paraben, butyl paraben, and LiquaPar oil (mixture of isobutyl paraben, isopropyl paraben, and butyl paraben).

Other Optional Components

Hair mousse compositions can further comprise additional surfactants. Such additional surfactants comprise nonionic, cationic, anionic, and other amphoteric surfactants which do not affect the foaming agent of the present invention. Non-limiting examples of such additional surfactants include sodium cocoyl isethionate (sodium cocoyl ethyl ester sulfonate), sodium fatty acid sarcosinate, sodium fatty acid methyl amino propionate, and Geropon TC42 (Na-N-cocoyl N-methyl taurate), lauric acid dimethanolamide. Additional surfactant is typically included at a level of less than 50%, preferably less than 33% of the foaming agent.

Hair mousse compositions may further comprise a variety of optional components. Such optional components include; thickeners and viscosity modifiers such as diethanolamides of long chain fatty acids, sodium chloride, and sodium sulfate, hair conditioning agents such as cetyl alcohol, stearyl alcohol, oleyl alcohol, and panthenol, ultraviolet absorbing agents such as octyl salicylate, pH adjusting agents such as citric acid, succinic acid, sodium hydroxide and triethanolamine, coloring agents, hair oxidizing agents such as hydrogen peroxide, perborate salts and persulfate salts, hair reducing agents such as thioglycolates, perfumes, perfume solubilizing agents such as polyethylene glycol fatty acid esters, sequestering agents, polymer plasticizing agents such as glycerin and propylene glycol, and volatile and non-volatile silicone fluids. Such optional ingredients are typically included at a level of 0.01–20%, preferably from 0.01–10% of the concentrate.

EXAMPLES

The following examples illustrate the compositions of the present invention, but are not intended to be limiting thereof. All percentages and ratios are described as active levels.

TABLE 1

| COMPONENT | AMOUNT (%) COMPOSITION NO. | | | |
|---|---|---|---|---|
| | 1 | 2 | 3 | 4 |
| Concentrate | 94.0 | 92.0 | 93.0 | 95.0 |
| Propellant L.P.G. | 6.0 | 8.0 | 7.0 | 5.0 |
| Total of Composition | 100.0 | 100.0 | 100.0 | 100.0 |
| COMPONENTS IN CONCENTRATE | | | | |
| Laureth-21[*1] | 0.08 | 0.16 | 0.14 | — |
| Laureth 4.2[*2] | 0.07 | 0.14 | 0.12 | 0.15 |
| Ceteth-15[*3] | 0.30 | 0.30 | — | — |
| Isosteareth-10[*4] | — | — | — | 0.05 |
| Oleth-2[*5] | — | — | 0.02 | — |
| PPG-5-Ceteth-20[*6] | — | — | — | 0.05 |
| PEG-40 hydrogenated castor oil[*7] | — | — | 0.05 | — |
| PEG-150 distearate[*8] | — | — | — | 0.05 |
| PPG-2 lanolin alcohol ether[*9] | — | — | 0.02 | — |
| Lauramide DEA[*10] | — | — | 0.03 | — |
| Polyquaternium 4 | 3.00 | 3.00 | — | 0.50 |
| Polyquaternium 7 | — | — | 6.25 | 10.00 |
| Polyquaternium 11 | — | 5.00 | 2.00 | — |
| Ethyl ether of PVM/MA copolymer | — | — | 0.33 | — |
| Ethanol | — | 10.00 | — | — |
| Methyl paraben | 0.15 | 0.15 | 0.15 | 0.15 |
| Propyl paraben | — | 0.05 | 0.05 | 0.05 |
| Phenoxyethanol | 0.25 | 0.15 | 0.15 | 0.15 |
| Disodium EDTA | 0.10 | 0.10 | 0.10 | 0.10 |
| Dimethicone copolyol | — | 0.17 | — | — |
| Perfume | 0.10 | 0.10 | 0.08 | 0.05 |
| Propylene glycol | 0.10 | — | — | — |
| DI water | q.s. | q.s. | q.s. | q.s. |
| Total of Concentrate | 100 | 100 | 100 | 100 |

TABLE 2

| COMPONENT | AMOUNT (%) COMPOSITION NO. | | | |
|---|---|---|---|---|
| | 5 | 6 | 7 | 8 |
| Concentrate | 91.0 | 94.0 | 100.0 | 93.0 |
| Propellant L.P.G. | 9.0 | 6.0 | 0.0 | 7.0 |
| Total of Composition | 100.0 | 100.0 | 100.0 | 100.0 |
| COMPONENTS IN CONCENTRATE | | | | |
| Laureth-21[*1] | — | 0.05 | 0.10 | 0.20 |
| Laureth-4.2[*2] | 0.10 | 0.15 | 0.05 | — |
| Ceteth-15[*3] | 0.14 | 0.05 | — | 0.05 |
| Isosteareth 10[*4] | — | — | 0.10 | — |
| Oleth-2[*5] | — | — | 0.02 | 0.05 |
| PPG-5-Ceteth-20[*6] | 0.02 | — | — | — |
| PEG-40 Hydrogenated castor oil[*7] | — | — | 0.03 | — |
| PEG-150 distearate[*8] | — | 0.05 | 0.03 | 0.03 |
| PPG-2 Lanolin alcohol ether[*9] | 0.02 | — | — | — |
| Polyquaternium 7 | — | 1.5 | 5.00 | — |
| Polyquaternium 10 | 1.00 | — | — | — |
| Polyquaternium 11 | — | 4.00 | 10.00 | — |
| Silicone grafted copolymer | — | — | — | 3.50 |
| Ethyl ether of PVM/MA copolymer | 0.25 | 1.00 | — | — |
| Ethanol | 3.00 | 4.00 | 10.00 | — |
| Methyl paraben | 0.10 | 0.10 | 0.10 | 0.10 |
| Propyl paraben | 0.10 | 0.10 | 0.10 | 0.10 |
| Phenoxyethanol | 0.25 | 0.25 | 0.25 | 0.25 |
| Disodium EDTA | 0.10 | 0.10 | 0.10 | 0.10 |
| Dimethicone copolyol | 0.10 | 0.10 | — | — |
| Perfume | 0.05 | 0.05 | 0.10 | 0.10 |
| Propylene glycol | 0.10 | 0.10 | 0.20 | 0.10 |
| DI water | q.s. | q.s. | q.s. | q.s. |
| Total of Concentrate | 100 | 100 | 100 | 100 |

TABLE 3

| COMPONENT | AMOUNT (%) COMPOSITION NO. | |
| --- | --- | --- |
| | A | B |
| Concentrate | 94.0 | 94.0 |
| Propellant L.P.G. | 6.0 | 6.0 |
| Total of Composition | 100.0 | 100.0 |
| COMPONENTS IN CONCENTRATE | | |
| Laureth-21*1 | — | 0.16 |
| Laureth 4.2*2 | — | 0.14 |
| Ceteth-15*3 | — | 0.30 |
| Cocamidopropyl betaine | 1.00 | — |
| Lauramine oxide | 1.00 | — |
| | — | — |
| | — | — |
| Isosteareth 10*4 | — | — |
| Lauramide DEA*10 | — | — |
| Polyquaternium 4 | 3.00 | 3.00 |
| Polyquaternium 7 | — | — |
| Polyquaternium 11 | 5.00 | 5.00 |
| Ethyl ether of PVM/MA copolymer | — | — |
| Ethanol | — | — |
| Methyl paraben | 0.15 | 0.15 |
| Propyl paraben | 0.15 | 0.15 |
| Phenoxyethanol | 0.25 | 0.25 |
| Disodium EDTA | 0.10 | 0.10 |
| Dimethicone copolyol | — | — |
| Perfume | 0.10 | 0.10 |
| Propylene glycol | 0.10 | 0.10 |
| DI Water | q.s. | q.s. |
| Total of Concentrate | 100 | 100 |

*1Active of Nikkol BL-21, Polyoxyethylene(21) lauryl ether (100% wax like solid)
21 is an average value of ethylene oxide.
*2Active of Nikkol BL-4.2, Polyoxyethylene(4.2) lauryl ether (100% liquid)
4.2 is an average value of ethylene oxide.
*3Active of Nikkol BC-15TX, Polyoxyethylene(15) cetyl ether (100% wax like solid)
15 is an average value of ethylene oxide.
*4Active of AROSURF 66 E10 (100% liquid)
10 is an average value of ethylene oxide.
*5Active of Brij 92, Polyoxyethylene(2) oleyl ether (100% liquid)
2 is an average value of ethylene oxide.
*6Active of Procetyl AWS, polyoxyethylene(5) Polyoxyethylene(20) cetyl ether
Each of the numbers is an average value.
*7Active of Nikkol HCO-40, Polyoxyethylene derivative of hydrogenated caster oil with an average of 40 moles of ethylene oxcide (100% solid)
*8Active of Atlas G-1821, Polyethylene glycol chester of stearic acid with an average of 150 moles of ethylene oxide (100% solid)
*9Active of Solulan PB-2, Polypropylene glycol ether of lanolin alcohol.
2 is an average value of ethylene oxide.
*10Active of STANDARMI AC LDS-RV (30% solution)

The compositions shown in Tables 1, 2 and 3 can be prepared by any conventional method well known in the art. A suitable method is as follows: Polymers and preservatives are added into distilled water under agitation at room temperature. The obtained mixture is heated up to 70–75° C. until homogenized. Other optional components are added to the heated mixture, and agitated until homogenized. The obtained mixture is allowed to cool to 30–40° C., and surfactants, perfume and other heat sensitive components are added. The obtained concentrate is packed into cans with propellant.

Evaluation of the Product of the Present Invention

Evaluation of a composition of the present invention has been done according to the following two methods by using the following test products (compositions A and B):

1. Test products:
(The formulations of the following test products are shown in Table 3.)
Composition A: A mousse composition which is an example of the composition of co-pending U. S. application Ser. No. 08/154231.
Composition B: A mousse composition which is an example of the present invention.

(1) FLAKING TENDENCY TEST

Method:

Prepare black, straight flat hair switches (Oriental-hair switches), total 10 gram weight per switch, with 7 cm width and 25 cm length. Hang the each hair switch upright on a stand, under room temperature condition. Weight 1.5 gram of mousse foam of the test products (A and B). Carefully spread out the foam on the surface of one side of switch, without letting the foam collapsing off while applying. Uniformly spread all 1.5 gram across whole hair switch and let the foam dry on switches naturally. After foam disappear and dry, grade the residue tendency using the following scale.

Scale: 0: Nothing visual. (Same as Virgin hair)
Scale 1: Slight residue.
Scale 2: Moderate residue.
Scale 3: Severe residue. (Same as Virgin hair)
Scale 4: Very severe residue.

The results of 10 expert panelists evaluation showed:
Composition A: Scale 3.0
Composition B: Scale 0.8

Namely, composition B showed significantly less flaking tendency than composition A.

(2) TEST FOR CLEARNESS OF CONCENTRATES

Method:

Put 5g concentrates into a 100 ml glass jar (diameter: 4 cm, height: 10 cm). Ask 10 panelists to rate the clearness of the concentrates based on the following scales:

0: Extremely clear.
1: Very clear
2: Clear
3: Not so clear/not so cloudy.
4: Cloudy
5: Very cloudy
6: Extremely cloudy.

The results of 10 panelists evaluation showed: composition A average score is 4.6, Standard Deviation is 0.84. composition B: average score is 1.2, standard deviation is 0.79.

Namely, the calculation of SD showed these results are significantly different. In other words, composition A is significantly clearer than composition B.

What is claimed is:

1. A cosmetic foaming composition, comprising 0.005–20 weight percent of a foaming agent and a solvent, the foaming agent comprising a mixture of first and second nonionic surfactants and having a total HLB as measured by the Griffin method of at least 12, the first nonionic surfactant being selected from the group consisting of a) a polyoxyethylene alkyl ether surfactant having the following general formula (I):

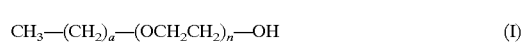

$$CH_3-(CH_2)_a-(OCH_2CH_2)_n-OH \qquad (I)$$

wherein a has an average value of from 9 to 21 and n has an average value of from 2 to 200;

b) a polyoxyethylene alkenyl ether surfactant having the following general formula (II):

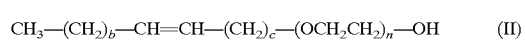

$$CH_3-(CH_2)_b-CH=CH-(CH_2)_c-(OCH_2CH_2)_n-OH \qquad (II)$$

wherein b has an average value of from 1 to 10, c has an average value of from 1 to 10, and n has an average value of from 2 to 200;

c) a polyoxypropylene polyoxyethylene ether surfactant having the following general formula (III):

$$R_1-(OCH(CH_3)CH_2)_x-(OCH_2CH_2)_y-OH \quad (III)$$

wherein $R_1$ is selected from the group consisting of alkyl alkenyl groups, iso-alkyl alkenyl groups and dimethylpolysiloxane groups, x has an average value of from 2 to 100, and y has an average value of from 2 to 100; and d) mixtures thereof; and the second nonionic surfactant being selected from the group consisting of:

e) a polyoxyethylene long chain alkyl fatty acid or benzene ether surfactant having the following general formula (IV):

$$R_2-(OCH_2CH_2)_n-OH \quad (IV)$$

wherein $R_2$ is selected from the group consisting of castor oil triglyceride castorate, cholesterol, coconut oil triglyceride cocoate, alkyl phenol, glyceryl laurate, glyceryl oleate, glyceryl cocoate, glyceryl isostearate, glyceryl stearate, hydrogenated castor oil triglyceride hydrogenated castorate, hydrogenated lanolin, nonyl phenyl and dimethylpolysiloxane groups, and n has an average value of from 2 to 200;

f) a polyoxyethylene ether surfactant having the following general formula (V):

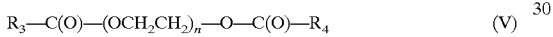

$$R_3-C(O)-(OCH_2CH_2)_n-O-C(O)-R_4 \quad (V)$$

wherein $R_3$ and $R_4$ are respectively selected from the group consisting of alkyl groups, iso-alkyl groups and alkenyl groups, and n has an average value of from 2 to 200;

g) a polyoxypropylene ether surfactant having the following general formula (VI):

$$R_5-(OCH(CH_3)CH_2)_n-OH \quad (VI)$$

wherein $R_5$ is selected from the group consisting of alkyl groups, iso-alkyl groups and alkenyl groups, and n has an average value of from 2 to 200; and h) mixtures thereof.

2. A hair mousse composition, comprising, by weight, 40–100% of a concentrate and 0–60% of a propellant the concentrate comprising, by weight:

a) 0.005–20% of a foaming agent comprising a mixture of first and second nonionic surfactants and having a total HLB as measured by the Griffin method of at least 12, the first nonionic surfactant being selected from the group consisting of (i) a polyoxyethylene alkyl ether surfactant having the following general formula (I);

$$CH_3-(CH_2)_a-(OCH_2CH_2)_n-OH \quad (I)$$

wherein a has an average value of from 9 to 21 and n has an average value of from 2 to 200;

(ii) a polyoxyethylene alkenyl ether surfactant having the following general formula (II):

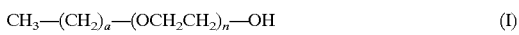

$$CH_3-(CH_2)_b-CH=CH-(CH_2)_c-(OCH_2CH_2)_n-OH \quad (II)$$

wherein b has an average value of from 1 to 10, c has an average value of from I to 10. and n has an average value of from 2 to 200:

(iii) a polyoxypropylene polyoxyethylene ether surfactant having the following general formula (III):

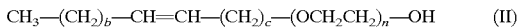

$$R_1-(OCH(CH_3)CH_2)_x-(OCH_2CH_2)_y-OH \quad (III)$$

wherein $R_1$ is selected from the group consisting of alkyl alkenyl groups iso-alkyl alkenyl groups and dimethylpolysiloxane derivatives, x has an average value of from 2 to 100 and y has an average value of from 2 to 100: and (iv) mixtures thereof; and the second nonionic surfactant being selected from the group consisting of:

(v) a polyoxyethylene long chain alkyl fatty acid or benzene ether surfactant having the following general formula (IV):

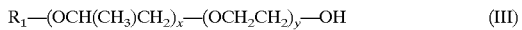

$$R_2-(OCH_2CH_2)_n-OH \quad (IV)$$

wherein $R_2$ is selected from the group consisting of castor oil triglyceride castorate cholesterol, coconut oil triglyceride cocoate, alkyl phenol, glyceryl laurate, glyceryl oleate, glyceryl cocoate, glyceryl isostearate, glyceryl stearate, hydrogenated castor oil triglyceride hydrogenated castorate, hydrogenated lanolin, nonyl phenyl and dimethylpolysiloxane derivatives, and n has an average value of from 2 to 200:

(vi) a polyoxyethylene ether surfactant having the following general formula (V):

$$R_3-C(O)-(OCH_2CH_2)_n-O-C(O)-R_4 \quad (V)$$

wherein $R_3$ and $R_4$ are respectively selected from the group consisting of alkyl groups, iso-alkyl groups and alkenyl groups, and n has an average value of from 2 to 200:

(vii) a polyoxypropylene ether surfactant having the following general formula (VI):

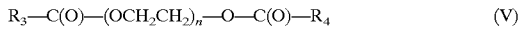

$$R_5-(OCH(CH_3)CH_2)_n-OH \quad (VI)$$

wherein $R_5$ is selected from the group consisting of alkyl groups, iso-alkyl groups and alkenyl groups, and n has an average value of from 2 to 200: and (viii) mixtures thereof; and b) 60–99% of a solvent.

3. The hair mousse composition according to claim 2, wherein the concentrate comprises, by weight:

i) 0.005–10% of the foaming agent;

ii) 80–99% of the solvent;

iii) 0–15% of a polymer selected from the group consisting of a cationic polymer, nonionic polymer, anionic polymer, amphoteric polymer, and mixtures thereof; and iv) 0–5% of a preservative.

4. The hair mousse composition according to claim 3, wherein the polymer is selected from the group consisting of quaternized cellulose ethers, quaternized vinyl pyrrolidone/alkylamino(meth)acrylate copolymers, methylvinylimidazolium vinylpyrrolidone quaternary ammonium copolymers, silicone-grafted copolymers, and mixtures thereof.

5. A hair mousse composition, comprising, by weight, 70–100% of a concentrate and 0–30% of a propellant, the concentrate comprising, by weight:

a) 0.005–0.5% of cosmetic foaming agent comprising a mixture of first and second nonionic surfactants and having a total HLB as measured by the Griffin method of at least 12, the first nonionic surfactant being selected from the group consisting of (i) a polyoxyethylene alkyl ether surfactant having the following general formula (I):

$$CH_3-(CH_2)_a-(OCH_2CH_2)_n-OH \quad (I)$$

wherein a has an average value of from 9 to 21 and n has an average value of from 2 to 200:

(ii) a polyoxyethylene alkenyl ether surfactant having the following general formula (II):

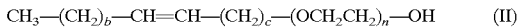

$$CH_3-(CH_2)_b-CH=CH-(CH_2)_c-(OCH_2CH_2)_n-OH \quad (II)$$

wherein b has an average value of from 1 to 10 c has an average value of from 1 to 10, and n has an average value of from 2 to 200:

(iii) a polyoxypropylene polyoxyethylene ether surfactant having the following general formula (III):

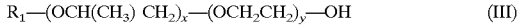

$$R_1-(OCH(CH_3)\ CH_2)_x-(OCH_2CH_2)_y-OH \quad (III)$$

wherein $R_1$ is selected from the group consisting of alkyl alkenyl groups, iso-alkyl alkenyl groups and dimethylpolysiloxane derivatives, x has an average value of from 2 to 100, and y has an average value of from 2 to 100: and (iv) mixtures thereof: and the second nonionic surfactant being selected from the group consisting of:

(v) a polyoxyethylene long chain alkyl fatty acid or benzene ether surfactant having the following general formula (IV):

$$R_2-(OCH_2CH_2)_n-OH \quad (IV)$$

wherein $R_2$ is selected from the group consisting of castor oil triglyceride castorate, cholesterol, coconut oil triglyceride cocoate, alkyl phenol, glyceryl laurate, glyceryl oleate, glyceryl cocoate, glyceryl isostearate, glyceryl stearate, hydrogenated castor oil triglyceride hydrogenated castorate, hydrogenated lanolin, nonyl phenyl and dimethylpolysiloxane derivatives, and n has an average value of from 2 to 200:

(vi) a polyoxyethylene ether surfactant having the following general formula (V): wherein $R_3$ and $R_4$ are respectively selected from the group consisting of alkyl groups iso-alkyl groups and alkenyl groups, and n has an average value of from 2 to 200:

(vii) a polyoxypropylene ether surfactant having the following general formula (VI):

$$R_5-(OCH(CH_3)CH_2)_n-OH \quad (VI)$$

wherein $R_5$ is selected from the group consisting of alkyl groups, iso-alkyl groups and alkenyl groups, and n has an average value of from 2 to 200; and (viii) mixtures thereof, b) 85–98% of a solvent;

c) 0–15% of a polymer selected from the group consisting of a cationic polymer, nonionic polymer, anionic polymer, amphoteric polymer, and mixtures thereof; and d) 0–3% of a preservative.

6. A cosmetic foaming composition, comprising:

i) 0.005–5 weight percent nonionic surfactant foaming agent having a total HLB as measured by the Griffin method of at least 12 and comprising a mixture of first and second nonionic surfactants, the first nonionic surfactant being selected from the group consisting of a) a polyoxyethylene alkyl ether surfactant having the following general formula (I):

$$CH_3-(CH_2)_a-(OCH_2CH_2)_n-OH \quad (I)$$

wherein a has an average value of from 9 to 21 and n has an average value of from 2 to 200;

b) a polyoxyethylene alkenyl ether surfactant having the following general formula (II):

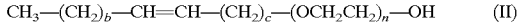

$$CH_3-(CH_2)_b-CH=CH-(CH_2)_c-(OCH_2CH_2)_n-OH \quad (II)$$

wherein b has an average value of from 1 to 10, c has an average value of from 1 to 10, and n has an average value of from 2 to 200;

c) a polyoxypropylene polyoxyethylene ether surfactant having the following general formula (III):

$$R_1-(OCH(CH_3)CH_2)_x-(OCH_2CH_2)_y-OH \quad (III)$$

wherein $R_1$ is selected from the group consisting of alkyl alkenyl groups iso-alkyl alkenyl groups and dimethylpolysiloxane groups x has an average value of from 2 to 100. and y has an average value of from 2 to 100; and d) mixtures thereof, and the second nonionic surfactant being selected from the group consisting of:

e) a polyoxyethylene long chain alkyl fatty acid or benzene ether surfactant having the following general formula (IV):

$$R_2-(OCH_2CH_2)_n-OH \quad (IV)$$

wherein $R_2$ is selected from the group consisting of castor oil triglyceride castorate, cholesterol, coconut oil triglyceride cocoate, alkyl phenol, glyceryl laurate, glyceryl oleate, glyceryl cocoate, glyceryl isostearate, glyceryl stearate, hydrogenated castor oil triglyceride hydrogenated castorate, hydrogenated lanolin nonyl phenyl and dimethylpolysiloxane groups and n has an average value of from 2 to 200;

f) a polyoxyethylene ether surfactant having the following general formula (V):

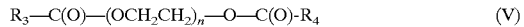

$$R_3-C(O)-(OCH_2CH_2)_n-O-C(O)-R_4 \quad (V)$$

wherein $R_3$ and $R_4$ are respectively selected from the group consisting of alkyl groups iso-alklyl groups and alkenyl groups, and n has an average value of from 2 to 200;

g) a polyoxypropylene ether surfactant having the following general formula (VI):

$$R_5-(OCH(CH_3)CH_2)_n-OH \quad (VI)$$

wherein $R_5$ is selected from the group consisting of alkyl groups, iso-alkyl groups and alkenyl groups, and n has an average value of from 2 to 200; and h) mixtures hereof; and ii) at least one additional surfactant selected from the group consisting of nonionic, cationic, anionic, and amphoteric surfactants, and mixtures thereof, wherein the additional surfactant is included at a level of less than 50%, by weight, of the nonionic surfactant foaming agent.

7. The cosmetic foaming composition according to claim 6, wherein the additional surfactant is selected from the group consisting of sodium cocoyl isethionate, sodium fatty acid sarcosinate, sodium fatty acid methyl amino propionate, sodium-N-cocyl N-methyl taurate, and lauric acid diethanolamide.

8. A hair mousse composition, comprising, by weight:

i) 40–100% a concentrate, said concentrate comprising, by weight:

a) 0.005–5% of nonionic surfactant foaming agent having a total HLB as measured by the Griffin method of at least 12 and comprising a mixture of first and second nonionic surfactants, the first nonionic surfactant being selected from the group consisting of 1) a polyoxyethylene alkyl ether surfactant having the following general formula (I):

$$CH_3-(CH_2)_a-(OCH_2CH_2)_n-OH \quad (I)$$

wherein a has an average value of from 9 to 21 and n has an average value of from 2 to 200;

2) a polyoxyethylene alkenyl ether surfactant having the following general formula (II):

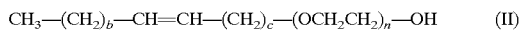  (II)

wherein b has an average value of from 1 to 10, c has an average value of from 1 to 10, and n has an average value of from 2 to 200:

3) a polyoxypropylene polyoxyethylene ether surfactant having the following general formula (III):

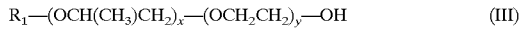  (III)

wherein $R_1$ is selected from the group consisting of alkyl alkenyl groups, iso-alkyl alkenyl groups and dimethylpolysiloxane groups x has an average value of from 2 to 100, and y has an average value of from 2 to 100; and 4) mixtures thereof; and the second nonionic surfactant being selected from the group consisting of:
5) a polyoxyethylene long chain alkyl fatty acid or benzene ether surfactant having the following general formula (IV):

  (IV)

wherein $R_2$ is selected from the group consisting of castor oil triglyceride castorate, cholesterol, coconut oil triglyceride cocoate, alkyl phenol, glyceryl laurate, glyceryl oleate, glyceryl cocoate, glyceryl isostearate, glyceryl stearate, hydrogenated castor oil triglyceride hydrogenated castorate, hydrogenated lanolin, nonyl phenyl and dimethylpolysiloxane groups, and n has an average value of from 2 to 200;

6) a polyoxyethylene ether surfactant having the following general formula (V):

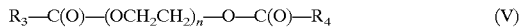  (V)

wherein $R_3$ and $R_4$ are respectively selected from the group consisting of alkyl groups iso-alkyl groups and alkenyl groups, and n has an average value of from 2 to 200;

7) a polyoxypropylene ether surfactant having the following general formula (VI):

  (VI)

wherein $R_5$ is selected from the group consisting of alkyl groups iso-alkyl groups and alkenyl groups, and n has an average value of from 2 to 200; and 8) mixtures thereof;

b) at least one additional surfactant selected from the group consisting of nonionic, cationic, anionic, and amphoteric surfactants, and mixtures thereof, wherein the additional surfactant is included at a level of less than 50%, by weight, of the nonionic surfactant foaming agent; and c) 60–99% of a solvent; and ii) 0–60% of a propellant.

9. The hair mousse composition according to claim 8, wherein the concentrate comprises, by weight, 0.005–5% of the nonionic surfactant foaming agent and 80–99% of the solvent, and wherein the concentrate further comprises (d) 0–15% of a polymer selected from the group consisting of a cationic polymer, nonionic polymer, anionic polymer, amphoteric polymer, and mixtures thereof; and (e) 0–5% of a preservative.

10. The hair mousse composition according to claim 9, wherein the polymer is selected from the group consisting of quatemized cellulose ethers, quaternized vinyl pyrrolidone/alkylamino(meth)acrylate copolymers, methylvinylimidazolium vinylpyrrolidone quaternary ammonium copolymers, silicone-grafted copolymers, and mixtures thereof.

11. A hair mousse composition according to claim 8, comprising, by weight:
i) 70–100% of the concentrate, wherein the concentrate comprises, by weight:
a) 0.005–0.5% of the nonionic surfactant foaming agent;
b) the least one additional surfactant at a level of less than 50%, by weight, of the nonionic surfactant foaming agent;
c) 85–98% of the solvent;
d) 0–15% of a polymer selected from the group consisting of a cationic polymer, nonionic polymer, anionic polymer, amphoteric polymer, and mixtures thereof; and
e) 0–3% of a preservative; and
ii) 0–30% of the propellant.

12. A hair mousse composition, comprising, by weight:
i) 70–100% of a concentrate, the concentrate comprising by weight:
a) 0.005–0.5% a cosmetic nonionic surfactant foaming agent having a total HLB as measured by the Griffin method of at least 12 and comprising a mixture of first and second nonionic surfactants, the first nonionic surfactant being selected from the group consisting of
1) a polyoxyethylene alkyl ether surfactant having the following general formula (I):

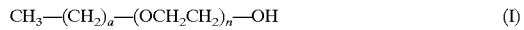  (I)

wherein a has an average value of from 9 to 21 and n has an average value of from 2 to 200;

2) a polyoxyethylene alkenyl ether surfactant having the following general formula (II):

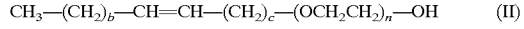  (II)

wherein b has an average value of from 1 to 10, c has an average value of from 1 to 10, and n has an average value of from 2 to 200;

3) a polyoxypropylene polyoxyethylene ether surfactant having the following general formula (III):

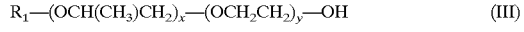  (III)

wherein $R_1$ is selected from the group consisting of alkyl alkenyl groups, iso-alkyl alkenyl groups and dimethylpolysiloxane groups x has an average value of from 2 to 100, and y has an average value of from 2 to 100; and 4) mixtures thereof; and the second nonionic surfactant being selected from the group consisting of:
5) a polyoxyethylene long chain alkyl fatty acid or benzene ether surfactant having the following general formula (IV):

  (IV)

wherein $R_2$ is selected from the group consisting of castor oil triglyceride castorate, cholesterol, coconut oil triglyceride cocoate, alkyl phenol, glyceryl laurate, glyceryl oleate, glyceryl cocoate, glyceryl isostearate, glyceryl stearate, hydrogenated castor oil triglyceride hydrogenated castorate, hydrogenated lanolin, nonyl phenyl and dimethylpolysiloxane groups, and n has an average value of from 2 to 200;

6) a polyoxyethylene ether surfactant having the following general formula (V):

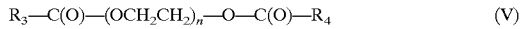

$$R_3-C(O)-(OCH_2CH_2)_n-O-C(O)-R_4 \quad (V)$$

wherein $R_3$ and $R_4$ are respectively selected from the group consisting of alkyl groups, iso-alkyl groups and alkenyl groups, and n has an average value of from 2 to 200;

7) a polyoxypropylene ether surfactant having the following general formula (VI):

$$R_5-(OCH(CH_3)CH_2)_n-OH \quad (VI)$$

wherein $R_5$ is selected from the group consisting of alkyl groups, iso-alkyl groups and alkenyl groups, and n has an average value of from 2 to 200; and 8) mixtures thereof;

b) 85–98% of a solvent;

c) 0–15% of a polymer selected from the group consisting of a cationic polymer, nonionic polymer, anionic polymer, amphoteric polymer, and mixtures thereof; and d) 0–3% of a preservative; and ii) 0–30% of a propellant.

13. The hair mousse composition according to claim 12, wherein the polymer is selected from the group consisting of quaternized cellulose ethers, quaternized vinyl pyrrolidone/alkylamino(meth)acrylate copolymers, methylvinylimidazolium vinylpyrrolidone quaternary ammonium copolymers, silicone-grafted copolymers, and mixtures thereof.

14. A method of styling hair, comprising applying to hair a cosmetic foaming composition according to claim 1.

15. A method of styling hair, comprising applying to hair a cosmetic foaming composition according to claim 6.

16. A method of styling hair, comprising applying to hair a hair mousse composition according to claim 12.

17. A method of styling hair, comprising applying to hair a cosmetic foaming composition according to claim 8.

* * * * *